United States Patent [19]

Cherkofsky et al.

[11] 4,159,338

[45] Jun. 26, 1979

[54] ANTIINFLAMMATORY-4,5-DICYCLIC-2-(SUBSTITUTED THIO)-IMIDAZOLES AND THEIR CORRESPONDING SULFOXIDES AND SULFONES

[75] Inventors: Saul C. Cherkofsky; Thomas R. Sharpe, both of Wilmington, Del.

[73] Assignee: E. I. Du Pont de Nemours and Company, Wilmington, Del.

[21] Appl. No.: 865,832

[22] Filed: Jan. 5, 1978

Related U.S. Application Data

[63] Continuation-in-part of Ser. No. 767,220, Feb. 9, 1977, abandoned.

[51] Int. Cl.$^2$ .................. A61K 31/415; A61K 31/44; C07D 405/02; C07D 409/04
[52] U.S. Cl. .................. 424/273 R; 424/263; 546/256; 546/278; 548/336; 548/337
[58] Field of Search .......................... 548/336, 337; 260/294.8 G, 294.8 R; 424/273 R, 263

[56] References Cited

U.S. PATENT DOCUMENTS

| | | | |
|---|---|---|---|
| 3,629,473 | 12/1971 | Doebel et al. | 260/294.8 G |
| 3,707,475 | 12/1972 | Lombardino | 260/294.8 R |
| 3,850,944 | 11/1974 | Tanaka et al. | 260/294.8 G |
| 3,929,807 | 12/1975 | Fitzi | 260/294.8 G |

OTHER PUBLICATIONS

Bhatt et al., I. Chem. Abst., 1948, vol. 42, col. 8799.
Bhatt et al., II Chem. Abst., 1954, vol. 48, col. 3967.
Fitzi, Chem. Abst., 1973, vol. 78, No. 58428x.
Lempert et al., Chem. Abst., 1965, vol. 63, col. 13238.
Zaur et al., Chem. Ber., 1973, vol. 106, pp. 1628–1636.

*Primary Examiner*—Richard Raymond

[57] ABSTRACT

Antiinflammatory 4,5-dicyclic-2-(substituted thio)-imidazoles and their corresponding sulfoxides and sulfones, such as, 4-(4-fluorophenyl)-2-(1,1,2,2-tetrafluoroethylsulfonyl)-5-(2-thienyl)-1H-imidazole, useful for treating arthritis and related diseases.

39 Claims, No Drawings

ANTIINFLAMMATORY-4,5-DICYCLIC-2-(SUBSTITUTED THIO)-IMIDAZOLES AND THEIR CORRESPONDING SULFOXIDES AND SULFONES

CROSS REFERENCE TO RELATED APPLICATIONS

This application is a continuation-in-part of prior application Ser. No. 767,220, filed Feb. 9, 1977, now abandoned.

BACKGROUND OF THE INVENTION

This invention relates to antiinflammatory imidazoles.

Lombardino, in U.S. Pat. No. 3,707,475 discloses antiinflammatory 4,5-diaryl-2-substituted imidazoles.

Doebel, in U.S. Pat. Nos. 3,505,350 and 3,651,080, respectively, discloses antiinflammatory 4-alkyl-5-aryl-1-substituted-2-mercapto-imidazoles and 4-alkyl-2-alkylthio-5-aryl-1-substituted imidazoles.

Zauer, K., et al., in *Chem. Ber.*, 106, 1638 (1973) disclose 4,5-bis(4-methoxyphenyl)-2-methylthioimidazole and 4,5-bis(4-chlorophenyl)-2-methylthioimidazole but do not suggest any use.

A number of references, such as *Current Sci. Inida*, 17, 184–85 (1948) and *Acta. Chem. Acad. Sci. Hung.*, 79 (2) 197–212 (1973) disclose 2-(substituted-thio)-4,5-diphenyl imidazoles with substituents such as methyl, propyl, allyl, and acetonyl.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and anti-inflammatory drugs are often used in their treatment. The usefulness of most commercial anti-inflammatories is limited because of toxicity and adverse side-effects. Many produce gastric irritation and other effects, such as changes in blood cells and central nervous system. Adreno-cortical steroids produce gastric irritation and suppression of normal adrenal function.

The present invention results from efforts to develop new anti-arthritic compounds with good anti-inflammatory activity and minimal side effects that could be more effective in treating arthritis than presently available drugs.

In addition to anti-inflammatory properties, some compounds of this invention have demonstrated analgesic activity in a test procedure. This additional property is desirable in treatment of arthritis or related diseases; however, such compounds can be employed solely to alleviate pain.

SUMMARY OF THE INVENTION

According to this invention there is provided compounds of formula I, pharmaceutical compositions containing them, and methods of using them to treat arthritis in mammals.

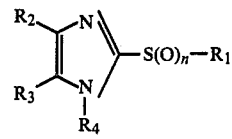

where
$n = 0$, 1, or 2;
$R_1$ = polyfluoro-$C_1$-$C_2$ alkyl;
$R_2$ and $R_3$, the same or different = 2-thienyl, 3-thienyl, 3-pyridyl, 3-pyridyl-N→oxide, 2-furyl or

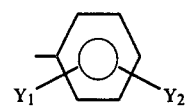

where
$Y_1$ and $Y_2$, the same or different = H, $C_1$-$C_4$ alkoxy, $C_1$-$C_4$ alkyl, Cl, F, or $Y_1$ and $Y_2$ taken together forming a dioxymethylene bridge,
provided that only one of $R_2$ or $R_3$ can =

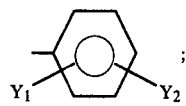

and
$R_4$ = hydrogen;

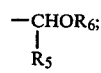

2-tetrahydropyranyl;
2-tetrahydrofuranyl;

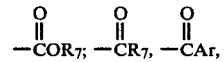

where
$R_5$ = H or methyl;
$R_6$ = $C_1$-$C_3$ alkyl, benzyl, —CH$_2$CH$_2$OCH$_3$

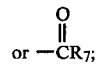

$R_7$ = $C_1$-$C_4$ alkyl or benzyl; and

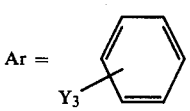

where
$Y_3$ = H, F, Cl, Br, $C_1$-$C_4$ alkyl, $C_1$-$C_4$ alkoxy, or nitro; provided when

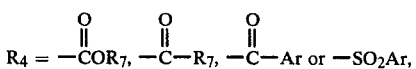

then n must be 0; or its pharmaceutically suitable acid addition salts where n=0 or where at least one of $R_2$ or $R_3$, independently, =3-pyridyl; and its pharmaceutically acceptable metal salts where $R_4$=hydrogen and n=1 or 2.

Tautomers

When $R_2$ and $R_3$ are different and $R_4$=hydrogen, the following two structures are tautomers:

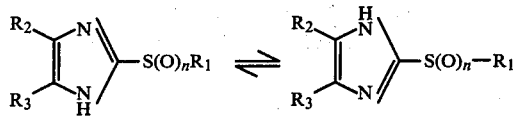

Pharmaceutical Salts

Pharmaceutically suitable acid addition salts of compounds where n=0 or where at least one of $R_2$ and $R_3$, independently, =3-pyridyl include those made with physiologically acceptable acids and such salts include hydrochloride, sulfate, phosphate and nitrate, Pharmaceutically suitable metal salts of compounds where $R_4$=hydrogen and n=1 or 2 include those of certain metals, such as sodium, potassium, and calcium.

DETAILED DESCRIPTION OF THE INVENTION

Preferred Compounds

Compounds preferred for their antiarthritic activity are those where $R_1$=—$CF_2CF_2H$, or —$CF_3$.

Also preferred are those compounds where $R_2$ and $R_3$, independently=2-thienyl or 3-pyridyl.

Also preferred are these compounds where $R_2$ or

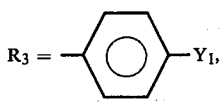

where $Y_1$=H, Cl, F or $CH_3O$.

Also preferred are those compounds where $R_4$=hydrogen, ethoxycarbonyl, benzyloxymethyl, acetyl, benzoyl, or 2-tetrahydrofuranyl More preferred are these compounds where:
$R_1$=$CF_2CF_2H$ or $CF_3$;
$R_2$ and $R_3$, independently=2-thienyl, 3-pyridyl or

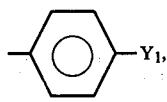

where $Y_1$=H, Cl, F or $CH_3O$, and provided that only one of $R_2$ or $R_3$

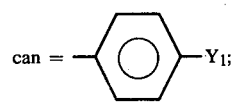

$Y_1$=H, Cl, F or $CH_3O$;
$R_4$=hydrogen, benzyloxymethyl, ethoxycarbonyl, acetyl, benzoyl, 2-tetrahydrofuranyl. Specifically preferred are the following compounds:

(a) 4-(4-fluorophenyl)-2-(1,1,2,2-tetrafluoroethylsulfonyl)-5-(2-thienyl)-1H-imidazole;
(b) 4-(4-fluorophenyl)-5-(2-thienyl)-2-trifluoromethylsulfonyl-1H-imidazole;
(c) 4-(4-methoxyphenyl)-5-(2-thienyl)-2-trifluoromethyl-sulfonyl-1H-imidazole;
(d) 4,5-bis-(2-thienyl)-2-(1,1,2,2-tetrafluoroethylsulfonyl)-1H-imidazole.
(e) 4-(4-methoxyphenyl)-2-(1,1,2,2-tetrafluoroethylsulfonyl)-5-(2-thienyl)-1H-imidazole;
(f) 4-(3,4-dichlorophenyl)-2-(1,1,2,2-tetrafluoroethylsulfonyl)-5-(2-thienyl)-1H-imidazole.

Synthesis

Compounds of formula I can be prepared as follows: a 4,5-dicyclic imidazole of the formula

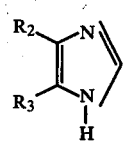

where $R_2$ and $R_3$ are defined above prepared as described in Brederick, H., et al., Chem. Ber., 86, 88 (1953) is reacted with sulfur at temperatures in the range of 150°–300° either with or without solvent to form a 2-mercaptoimidazole. One suitable solvent for this reaction is tetramethylene sulfone. This procedure is analogous to the conversion of 1-methylbenzimidazole to 2-mercapto-1-methylbenzimidaoole as described in A. V. El'tsov and K. M. Krivozheiko, Zh.Or.Kh. 2, 189 (1966).

4,5-Disubstituted-2-mercaptoimidazoles can also be prepared by reaction of compounds of the type

[$R_2$ and $R_3$ are described above; various syntheses of compounds of this type are described in Ide, W. S. and Buck, J. S., Organic Reactions, Vol. IV, p. 269] with thiourea in refluxing dimethylformamide or other high-boiling, polar solvents. A similar condensation procedure is described in Kochergin, P. M., Zhur. Obshchei Khim., 31, 1093 (1961); Chem. Abstr. 55, 23503F.

Preferably, reaction of the acyloins above with ammonium thiocyanate at lower temperatures in polar solvents such as ethanol or 1-propanol can be used to prepare 4,5-disubstituted-2-mercaptoimidazoles.

The appropriate $R_1$ group can be introduced with a suitable alkylating agent such as tetrafluoroethylene, difluorocarbene or 2,2,2-trifluoroethyltrichloromethane sulfonate. Similar addition reactions are described in England, D.C., et al., J. Am. Chem. Soc., 82, 5116 (1960) and Rapp, K. E., et al., J. Am. Chem. Soc., 72, 3642 (1950). For the purpose of this disclosure tetrafluoroethylene and other fluorinated olefins used are considered alkylating agents.

In certain instances a polyhaloalkyl moiety can be further modified chemically in forming the $R_1$ constituent of Formula I. For example, imidazoles containing the 2-(2-bromo-1,1,2-trifluoroethylthio) substituent can be converted to 2-(1,1,2-trifluoroethylthio)imidazoles by reduction with tri-n-butyltin hydride or other suitable reducing agents.

The imidazoles of the types:

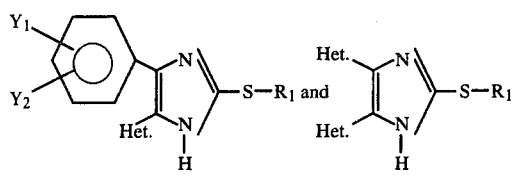

(where Het.=heterocyclic defined by $R_2$ and $R_3$ of formula I) can be oxidized to the corresponding sulfoxide or sulfone by using oxidizing agents such as m-chloroperoxybenzoic acid, Tweit, R.C., et al., *J. Med. Chem.*, 16, 1161 (1973), sodium metaperiodate, Leonard, N. V. and Johnson, C. R., *J. Org. Chem.*, 27, 282 (1962), hydrogen peroxide, Kochergin, P. M. and shchukina, M. N. *Gen. Chem.*, U.S.S.R., 25, 2289 (1955) or potassium permanganate, Rapp, K. E., et al., loc. cit.

When $R_2$ or $R_3$ of formula I are pyridyl, the oxidation can convert the pyridyl group to the N-oxide as the —S— is converted to sulfoxide or sulfone. In such a case, the 3-pyridyl-N-oxide group can be converted back to the free 3-pyridyl group by treating with a mild reducing agent such as a trialkoxy phosphite or triphenyl phosphine or tri-n-butyl phosphine or other mild reducing agent without reducing the sulfone function.

The appropriate $R_4$ substituent can often be introduced by direct alkylation, acylation, or sulfonylation of the compounds of formula I where $R_4$=H. This reaction can be carried in the absence or presence of a base, such as potassium carbonate, pyridine, triethylamine, potassium t-butoxide, methyl lithium or the like. The reaction can be run neat, using the reagent as solvent, or in the presence of an inert solvent, including but not limited to dimethylformamide, glyme, THF, pyridine, methylene chloride. The temperature of the reaction can be in the range $-78°$ C. to the boiling point of the solvent or reagent, if used in excess as the solvent. Examples of alkylating, acylating and sulfonylating agents that can be employed are alkoxymethyl halides, such as benzyloxymethyl chloride; acyloxymethyl halides, such as chloromethylpivalate; dihydropyran; 2-chlorotetrahydrofuran; alkyl chloroformates, such as ethyl chloroformate; alkanoic anhydrides and alkanoyl halides, such as acetic anhydride; aroyl halides, such as benzoyl chloride; arylsulfonyl halides, such as benzenesulfonyl chloride.

Alternatively, the $R_4$-substituent other than hydrogen of formula I can be introduced by first reacting a 4,5-disubstituted imidazole with an appropriate reagent such as benzyl chloromethyl ether, 2-chlorotetrahydrofuran, dihydropyran, or benzenesulfonyl chloride. The resulting 4,5-disubstituted-1-(substituted)imidazole is then treated with a strong base, such as n-butyl lithium, followed by a fluorinated alkylsulfenyl halide, disulfide, or sulfonic anhydride. Typical of these reagents are $CF_3SCl$, $CF_3SSCF_3$, and $(CF_3SO_2)_2O$. Optionally, the choice of the protecting group and the workup conditions allows isolation of the desired 4,5-cyclic-2-(substituted thio or sulfonyl)imidazole with $R_4$=H directly. Compounds where $R_1$=$CF_3$ can be conveniently prepared by this method.

Preparation of pharmaceutically suitable salts of formula I can be in accordance with well-known techniques of forming salts.

The preparation of these compounds is further illustrated by the following examples. Parts are by weight and temperatures are in centigrade unless otherwise specified.

EXAMPLE 1

2-[(1,1,2,2-Tetrafluoroethyl)thio]-4,5-bis-(2-thienyl)-1H-imidazole

(A) 4,5-bis-(2-Thienyl)-1H-imidazole

A mixture of 31.6 g of α-thienoin and 175 ml of formamide was refluxed while stirring beneath an air condenser for two hours. The resulting dark solution was poured into 600 ml of cold water, stirred and filtered. The product was a semi-solid which slowly hardened; yield 27.6 g. This was dissolved in 35 ml of hot dimethylformamide. The product crystallized on cooling, and was filtered and washed with dimethylformamide and acetonitrile. The yield was 11.1 g, m.p. 218°221.5° C. A further quantity of product was isolated from the filtrates by chromatography on alumina.

(B) 4,5-bis(2-Thienyl)-1H-2-imidazolethiol

A mixture of 12 g of 4,5-bis-(2-thienyl)-1H-imidazole, 250 ml of tetramethylene sulfone (purified), and 2.5 g of sulfur was heated at 170° C. for 24 hours in a nitrogen atmosphere, then 2 g more sulfur was added and the heating continued 19 hrs. The mixture was cooled, poured into 2 l. water, filtered, washed and dried. The dried product (9.8 g) was dissolved in dimethylformamide and poured on a column of alumina and eluted with dimethylformamide. The product came off with the first cuts, and after evaporating and stirring with acetonitrile and filtering, 5.3 g of product was obtained, melting 213°–218°. A thin layer chromatograph shows this to be a mixture of the starting material and the desired thiol. A small portion of the crude compound chromatographed in the same way gave 1.02 g, m.p. 283°–290° C.

Alternatively, a mixture of 27.9 g (0.25 mole) of 2-thienoin and 13.3 g of ammonium thiocyanate in 150 ml of 1-propanol was heated at reflux overnight, cooled and then 22.7 g of 4,5-bis(2-thienyl)-1H-2-imidazolethiol was collected by filtration, m.p. 294°–303° (dec.) (Recrystallized from 1-butanol).

Anal.Calc'd. for $C_{11}H_8N_2S_3$: C, 50.00; H, 3.03; N, 10.61. Found: 50.15; H, 3.15; N, 10.73.

(C)

2-[(1,1,2,2-Tetrafluoroethyl)thio]-4,5-bis(2-thienyl)-1H-imidazole

A 6.0-g portion of the above products was dissolved in 50 ml of dimethylformamide and 2 ml of diisopropyl amine and placed in a bomb tube and pressured with 5 g of tetrafluoroethylene. The pressure was 220 psi and on shaking dropped to 162 psi in 23 minutes. The temperature was in the range 25°–28° C. The bomb was shaken for 4.5 hrs. longer and the pressure remained unchanged. The dimethylformamide solution was removed from the bomb tube, poured into water, the product filtered and washed with water - yield 6.9 g, m.p. 131.5°–142° C. This was chromatographed on a silica gel column (Silicar CC-4) and eluted with chloroform to yield 3.1 g, m.p. 161.5°–163.5° C. Recrystallization from toluene gave an analytical sample, m.p. 166°–7°. Anal. Calcd for $C_{13}H_8F_4N_2S_3$: C, 42.86; H, 2.20; N, 7.69. Found: C, 42.86; H, 2.28; N, 7.76.

EXAMPLE 2

4-(4-Fluorophenyl)-2-(1,1,2,2-tetrafluoroethylthio)-5-(2-thienyl)-1H-imidazole

(A) 2-Dimethylamino-2-(2-thienyl)acetonitrile

A solution of 131.5 g. of dimethylamine hydrochloride in 200 ml of water was stirred and 59 g of sodium cyanide added. A solution of 112 g of 2-thiophenecarboxaldehyde in 100 ml of methanol was added from a dropping funnel while the temperature was kept below 30° C. The mixture was then maintained at 30° C. for 4 hours; it was then poured into 3 l. of water.

The water was extracted with ether, the ether extract was washed with water, saturated sodium bisulfite solution and last by water. The ether was dried over anhydrous magnesium sulfate and concentrated to give 156.5 g of yellow oil.

(B) 2-(4-Fluorophenyl)-1-(2-thienyl)ethanone

A suspension of 15 g sodium hydride in 250 ml of dimethylformamide was stirred as 83.1 g of 2-dimethylamino-2-(2-thienyl)acetonitrile in 300 ml of dimethylformamide was added. The mixture was stirred 1 hr. and $H_2$ was evolved. To this stirred mixture was added 72.3 g of 4-fluorobenzyl chloride over a period of 1 hr. The temperature rose to 50° C. during the addition and the mixture was kept at 40°–45° C. for an additional hour. The mixture was partially concentrated under reduced pressure, poured into 500 ml of water; to this was added 500 ml of chloroform and 500 ml of concentrated hydrochloric acid. The mixture was stirred and refluxed 24 hrs., cooled and separated. The water layer was extracted three times with chloroform and the chloroform extracts combined and dried over anhydrous potassium carbonate. The dried extract was filtered and concentrated to give 103.9 g of dark oil. This was distilled at 0.2 mm to give 72.4 g of product, m.p. 60°–62°C.

Alternatively, to a mixture of 75.0 g (0.5 mole) of 4-fluorophenylacetic acid and 195.0 g of thiophene warmed to 40° C. was added dropwise 111.0 g (0.65 mole) of trifluoroacetic anhydride. The reaction mixture was heated at reflux for 3 hours, cooled and then poured into ice. The aqueous layer was made basic with sodium carbonate and the product was extracted into ether. The combined ether extracts were washed with water and, after drying over anhydrous potassium carbonate, were evaporated to give 112.0 g of an oil. Crystallization from methanol afforded 70.0 g of 2-(4-fluorophenyl)-1-(2-thienyl)ethanone, m.p. 61°–2.5°.

Anal. Calc'd. for $C_{12}H_9FOS$: C, 65.45; H, 4.09; Found: C, 65.45; H, 4.06.

(C) 2-Bromo-2-(4-fluorophenyl)-1-(2-thienyl)ethanone

A solution of 71 g of 2-(4-fluorophenyl)-1-(2-thienyl)-ethanone in 300 ml of chloroform was added to 160 g of cupric bromide suspended in 500 ml of ethyl acetate while the mixture was refluxing. Refluxing was continued 2 hrs. after the addition, and the mixture was cooled, filtered and dried over anhydrous potassium carbonate. The mixture was filtered and concentrated to give 96.0 g of residue which was used without further purification.

(D) 4-(4-Fluorophenyl)-5-(2-thienyl)-1H-imidazole

A mixture of 2-bromo-2-(4-fluorophenyl)-1-(2-thienyl)-ethanone and 400 ml of formamide was refluxed beneath an air condenser for 2 hrs. It was poured into 1.5 l. of water and ice and the product filtered and dried—yield 41.2 g. This was chromatographed on 500 g of neutral alumina (Woelm activity grade I) using dimethylformamide as the solvent and eluant. The first cuts were diluted with ethyl acetate and filtered to give 19.2 g. This was recrystallized from acetonitrile to give 14.8 g, m.p. 163°–164.5° C., which after drying in vacuum oven overnight melted 198.5°–200° C. A further workup of filtrates gave 4.5 g more solid, m.p. 197°–198° C. The combined solids were crystallized from 350 ml of acetonitrile to give 16.4 g, m.p. 199°–200° C.

(E) 2-(4-Fluorophenyl)-2-hydroxy-1-(2-thienyl)ethanone.

To a solution of 70.0 g (0.32 mole) of 2-(4-fluorophenyl-1-(2-thienyl)ethanone in 600 ml of ether was added dropwise a solution of 56.0 g (0.35 mole) of bromine in 120 ml of methylene chloride at room temperature. The reaction mixture was concentrated under vacuum to give 123.0 g of 2-bromo-2-(4-fluorophenyl)-1-(2-thienyl)ethanone as an oil.

A solution of the residual oil above in 275 ml of ethanol was added to a solution of 1 mole of sodium ethoxide in 1 l of ethanol and the mixture stirred overnight at room temperature. The reaction mixture was poured onto 3 l of 0.3 M ice-water to give 63.4 g of 2-(4-fluorophenyl)-2-hydroxy-1-(2-thienyl)ethanone m.p. 90°–2°.

(F) 4-(4-Fluorophenyl)-5-(2-thienyl)-1H-2-imidazolethiol

A mixture of 16.0 g of 4-(4-fluorophenyl)-5-(2-thienyl)-1H-imidazole and 4 g of sulfur in 100 ml of tetramethylene sulfone (redistilled) was heated to 200° C. for 8 hrs., cooled, poured into water and filtered and dried. This was chromatographed by dissolving it in 125 ml of dimethylformamide and passing it over a neutral alumina (Woelm activity grade 1) column 60 mm in diameter and 200 mm long. A bright yellow band led the dark-colored bands giving cuts which were combined and concentrated—yield about 20 g. This was stirred with ethyl acetate and filtered—yield 14.3 g, m.p. 228°–237° C. This is a dimethylformamide solvate of the product.

Alternatively, reaction of 63.4 g (0.27 mole) of 2-(4-fluorophenyl)-2-hydroxy-1-(2-thienyl)ethanone with 29.0 g (0.38 mole) of ammonium thiocyanate in 1-propanol gave 71.6 g of 4-(4-fluorophenyl)-5-(2-thienyl)-1H-2-imidazolethiol, m.p. 275°–277° (Recrystallized from 1-butanol).

Anal. Calc'd. for $C_{13}H_9FN_2S_2$: C, 56.52; H, 3.26; N, 10.14. Found: C, 56.55; H, 3.42; N, 10.18.

(G) 4-(4-Fluorophenyl)-2-(1,1,2,2-tetrafluoroethylthio)-5-(2-thienyl)-1H-imidazole.

A solution of 14.0 g of 4-(4-fluorophenyl)-5-(2-thienyl)-1H-2-imidazolethiol in 40 ml of dimethylformamide and 1.5 g of diisopropylamine was pressured in a bomb with 4 g of tetrafluoroethylene. The pressure dropped from 160 psi to 0 in 1.5 hrs. The solution was poured into water, stirred until most of gum solidified, filtered and washed with water. The solid was dissolved in chloroform, dried over anhydrous sodium sulfate, concentrated and diluted with 1-chlorobutane. The crystalline product was collected; yield 2.5 g, m.p. 164°–168° C. The residue from the filtrate was chromatographed on silica gel (Silicar CC-4) using chloroform to give 4.1 g, m.p. 167.5°–170° C. The combined 6.5 g was crystallized from 1-chlorobutane to give 5.6 g, m.p. 167°–168.5° C.

Anal. Calc'd. for $C_{15}H_9F_5N_2S_2$: C, 47.87; H, 2.39; N, 7.45; Found: C, 48.24; H, 2.58; N, 7.83.

EXAMPLE 3

4-(4-Fluorophenyl)-2-(1,1,2,2-tetrafluoroethylsulfonyl)-5-(2-thienyl)-1H-imidazole A mixture of 6.5 g of 4-(4-fluorophenyl)-2-(1,1,2,2-tetrafluoroethylthio)-5-(2-thienyl)-1H-imidazole in 160 ml of chloroform was stirred as 9 g of 85% m-chloroperoxybenzoic acid was added. Slight warming was noted. The mixture was allowed to stand two days, then 30 ml of dimethyl sulfide was added, and warming was again noted. The mixture was cooled and filtered, and the filtrate was stirred with water and the water phase made basic with sodium bicarbonate. The organic layer was separated, dried over sodium sulfate and concentrated. The solid was taken up in 40 ml of hot 1-chlorobutane, treated with activated charcoal (Darco), filtered and concentrated to ⅓ volume. Crystals separated; yield 2.1 g, m.p. 192°–193° C.

Anal. Calc'd. for $C_{15}H_9F_5N_2O_2S_2$: C, 44.11; H, 2.22; N, 6.86. Found: C, 44.55; H, 2.46; N, 7.04.

EXAMPLE 4

4-(4-Chlorophenyl)-2-(1,1,2,2-tetrafluoroethylthio)-5-(2-thienyl)-1H-imidazole (A) 2-(4-Chlorophenyl)-1-(2-thienyl)ethanone A mixture of 85.3 g of p-chlorophenylacetic acid and 200 ml of thiophene was stirred at 40° C. as 105 g of trifluoroacetic anhydride was added. The mixture was then refluxed for 4 hrs. It was poured into ice and water and made basic with sodium carbonate. The mixture was extracted with dichloromethane, dried over potassium carbonate and concentrated. The crude yield was 126.4 g. This was recrystallized from 300 ml of methanol to give 103 g, m.p. 98°–99° C.

(B) 2-Bromo-2-(4-chlorophenyl)-1-(2-thienyl)ethanone

A solution of 100 g of 2-(4-chlorophenyl)-1-(2-thienyl)-ethanone in 400 ml of chloroform was added to a refluxing suspension of 200 g of cupric bromide in 650 ml of ethyl acetate. At the end of the addition, the mixture was refluxed three hours. The mixture was cooled in an ice bath, then filtered and the filtrate stirred with ice and water. The solution was brought to a neutral pH by adding sodium bicarbonate. The organic layer was separated and the water extracted two times with chloroform. The combined extracts were dried over anhydrous potassium carbonate, filtered and concentrated; yield 142 g. This product was used without further purification.

(C) 4-(4-Chlorophenyl)-5-(2-thienyl)-1H-imidazole

A mixture of 35 g of 2-bromo-2-(4-chlorophenyl)-1-(2-thienyl)ethanone and 200 ml of formamide was refluxed under an air condenser for two hours. It was cooled, poured into water and the pH adjusted to 8–9 by adding ammonium hydroxide. Chloroform was added to the solution, and solid separated and was filtered and washed with chloroform; yield 19.3 g. This was recrystallized from dimethylformamide, filtered and washed with acetonitrile; yield 14.7 g, m.p. 244°–245° C.

(D) 4-(4-Chlorophenyl)-5-(2-thienyl)-1H-2-imidazolethiol

A mixture of 9.4 g of 4-(4-chlorophenyl)-5-(2-thienyl)-1H-imidazole, 2 g of sulfur, and 50 ml of tetramethylene sulfone was stirred under nitrogen and heated to 200° C. for 8 hrs. It was cooled, poured into water, filtered and washed well with water to give 11.5 g. This was dissolved in dimethylformamide and chromatographed on a column 6 cm diameter by 125 cm long of alumina (Woelm neutral activity grade 1) using dimethylformamide to elute. A yield of 5.6 g was obtained as the dimethylformamide adduct. A sample was dried by heating under a high vacuum, m.p. 274.5°–276° C.

(E) 4-(4-Chlorophenyl)-2-(1,1,2,2-tetrafluoroethylthio)-5-(2-thienyl)-1H-imidazole.

A solution of 6.9 g of 4-(4-chlorophenyl)-5-(2-thienyl)-1H-2-imidazolethiol in 40 ml of dimethylformamide and 1.5 ml of diisopropylamine was pressured in a bomb with 3 g of tetrafluoroethylene and shaken until there was no further pressure drop. The bomb contents were poured into water, the pH adjusted to 8 and the solution extracted with chloroform. The extract was dried and concentrated. It was chromatographed on silica gel (Silicar CC-4) to give 5.5 g of a cut which was dissolved in hot 1-chlorobutane. On cooling 4.5 g of product was obtained, m.p. 161.5°–163° C.

Anal. Calc'd. for $C_{15}H_9ClF_4N_2S_2$: C, 45.86; H, 2.31; N, 7.13; S, 16.33. Found: C, 46.06; H, 2.49; N, 7.40; S, 16.44.

EXAMPLE 5

2-(1,1,2,2-Tetrafluoroethylsulfonyl)-4,5-bis-(2-thienyl)-1H-imidazole

A solution of 19 g of 2-[(1,1,2,2-tetrafluoroethyl)-thio]-4,5-bis-(2-thienyl)-1H-imidazole in 100 ml of chloroform was stirred as 2.3 g of m-chloroperoxybenzoic acid was added. The solution turned dark green. The mixture was allowed to stand at ambient temperature one week at which time 2 g more m-chloroperoxybenzoic acid was added and the mixture allowed to stand overnight.

The excess oxidant was then removed by stirring and adding 10 ml of methyl sulfide, stirring 1 hr. and concentrating. The residue was stirred with ether, filtered to remove an insoluble solid which was not the desired product. The ether filtrate was concentrated, the residue dissolved in chloroform, over-layered with aqueous potassium bicarbonate, and stirred, separated and concentrated—yield 1 g. This was chromatographed on a silica gel column (Silicar CC-4 3 cm diameter by 27 cm long) to give a product which was crystallized from ethyl acetate, washed with 1-chlorobutane; yield 0.282 g, m.p. 163°–165° C. A second crop of 0.196 g was obtained from the filtrate.

In another experiment, 4.0 g (11 mmoles) of 2-(1,1,2,2-tetrafluoroethylthio)-4,5-bis-(2-thienyl)-1H-imidazole was oxidized at ice-bath temperatures with 7.3 g (34.8 mmoles) 82.2% m-chloroperbenzoic acid in methylene chloride. m-Chlorobenzoic acid was removed by filtration and the filtrate was washed with 10% aqueous sodium bicarbonate solution. The methylene chloride solution was dried over anhydrous potassium carbonate and evaporated to yield 3.2 g of an oil, which was crystallized with 1-chlorobutane. Recrystallization from toluene: ethyl acetate gave 1.5 g of 2-(1,1,2,2-tetrafluoroethyl sulfonyl)-4,5-bis-(2-thienyl)-1H-imidazole; mass spectrum=396.

An analytical sample was prepared by chromatography on Silicar CC No. 7 with chloroform, m.p. 167-8.

Anal. Calc'd. for $C_{13}H_8F_4N_2O_2S_3$: C, 39.39; H, 2.02; N, 7.07. Found: C, 40.06; H, 2.06; N, 7.42.

EXAMPLE 6

4-(3,4-Dichlorophenyl)-2-(1,1,2,2-tetrafluoroethylthio)-5-(2-thienyl)-1H-imidazole.

(A) 2-(3,4-Dichlorophenyl)-1-(2-thienyl)ethanone.

Using the procedure described in Example 4A, 100.0 g of 3,4-dichlorophenylacetic acid, 242.0 g of thiophene and 144.0 g of trifluoroacetic anhydride gave from methanol 61.7 g of 2-(3,4-dichlorophenyl)-1-(2-thienyl)ethanone, m.p. 59.5-60.5.

Anal. Calc'd. for $C_{12}H_8Cl_2OS$: C, 53.14; H, 2.95. Found: C, 53.24; H, 2.95.

(B) 2-(3,4-Dichlorophenyl)-2-hydroxy-1-(2-thienyl)-ethanone 2-(3,4-Dichlorophenyl)-1-(2-thienyl)ethanone (57.0 g; 0.21 mole) was converted to 49.8 g of 2-(3,4-dichlorophenyl)-2-hydroxy-1-(2-thienyl)ethanone, m.p. 108°-9° (recrystallized from 1-chlorobutane) by the procedure described in Example 2E.

Anal. Calc'd. for $C_{12}H_8Cl_2O_2S$: C, 50.17; H, 2.99. Found: C, 50.34; H, 2.86.

(C) 4-(3,4-Dichlorophenyl)-5-(2-thienyl)-1H-2-imidazolethiol.

By the procedure described in the second paragraph of Example 2F, 45.0 g (0.16 mole) of 2-(3,4-dichlorophenyl)-2-hydroxy-1-(2-thienyl)ethanone was reacted with ammonium thiocyanate in 1-propanol at reflux to afford 32.6 g of 4-(3,4-dichlorophenyl)-5-(2-thienyl)-1H-2-imidazolethiol m.p. 263°-5°. (recrystallized from 1-butanol).

Anal. Calc'd. for $C_{13}H_8Cl_2N_2S_2 \cdot \frac{1}{2}H_2O$: C, 46.42; H, 2.69; N, 8.33. Found: C, 46.10; H, 2.82; N, 8.23.

(D) 4-(3,4-Dichlorophenyl)-2-(1,1,2,2-tetrafluoroethylthio)-5-(2-thienyl)-1H-imidazole.

4-(3,4-Dichlorophenyl)-5-(2-thienyl)-1H-2-imidazolethiol (30.0 g; 92 mmoles) was reacted with 15.0 g of tetrafluoroethylene as described in Example 4 E to give, after chromatography on Silicar CC No. 7 with chloroform, 19.1 g of 4-(3,4-dichlorophenyl)-2-(1,1,2,2-tetrafluoroethylthio)-5-(2-thienyl)-1H-imidazole, m.p. 178°-180° (recrystallized from toluene).

Anal. Calc'd. for $C_{15}H_8F_4Cl_2N_2S_2$: C, 42.15; H, 1.87; N, 6.56. Found: C, 42.88; H, 2.03; N, 6.57.

EXAMPLE 7

4-(3,4-Dichlorophenyl)-2-(1,1,2,2-tetrafluoroethylsulfonyl)-5-(2-thienyl)-1H-imidazole 4-(3,4-Dichlorophenyl)-2-(1,1,2,2-tetrafluoroethylthio)-5-(2-thienyl)-1H-imidazole (5.0 g; 11.7 mmoles) was oxidized with 6.1 g (29 mmoles) of 82.2% m-chloroperbenzoic acid according to the procedure described in the second paragraph of Example 5 and the crude product was purified by chromatography on Silicar CC No. 7 with chloroform to afford 1.4 g of 4-(3,4-dichlorophenyl)-2-(1,1,2,2-tetrafluoroethylsulfonyl)-5-(2-thienyl)-1H-imidazole, m.p. 158°-159.5° (recrystallized from toluene).

Anal. Calc'd. for $C_{15}H_8Cl_2F_4N_2O_2S_2$: C, 39.2; H, 1.74; N, 6.1. Found: C, 39.83; H, 1.96; N, 6.07.

EXAMPLE 8

4-(4-Methoxyphenyl)-2-(1,1,2,2-tetrafluoroethylthio)-5-(2-thienyl)-1H-imidazole

A series of reactions similar to those described in Example 6 using 4-methoxyphenylacetic acid gave the compounds below.

(A) 2-(4-Methoxyphenyl)-1-(2-thienyl)ethanone m.p. 75°-7° (recrystallized from methanol).

Anal. Calc'd. for $C_{13}H_{12}O_2S$: C, 67.24, H, 5.17. Found: C, 67.11; H, 5.29.

(B) 2-(4-Methoxyhenyl)-2-hydroxy-1-(2-thienyl)ethanone. m.p. 69°-73° (recrystallized from 1-chlorobutane)

Anal. Calc'd. for $C_{13}H_{12}O_3S$: C, 62.90; H, 4.84. Found: C, 62.15; H, 4.78.

(C) 4-(4-Methoxyphenyl)-5-(2-thienyl)-1H-2-imidazolethiol m.p. 266-268: (recrystallized from ethanol)

Anal. Calc'd. for $C_{14}H_{12}N_2OS_2$: C, 58.33; H, 4.17; N, 9.72. Found: C, 58.37; H, 4.27; N, 9.49.

(D) 4-(4-Methoxyphenyl)-2-(1,1,2,2-tetrafluoroethylthio)-5-(2-thienyl)-1H-imidazole. m.p. 112°-113.5° (chromatographed on Silicar CC No. 7 with chloroform and recrystallized from 1-chlorobutane).

Anal. Calc'd. for $C_{16}H_{12}F_4N_2OS_2$: C, 49.48; H, 3.09; N, 7.22. Found: C, 49.92; H, 3.21; N, 7.21.

EXAMPLE 9

4-(4-Methoxyphenyl)-2-(1,1,2,2-tetrafluoroethylsulfonyl)-5-(2-thienyl)-1H-imidazole 4-(4-Methoxyphenyl)-2-(1,1,2,2-tetrafluoroethylthio)-5-(2-thienyl)-1H-imidazole (4.0 g; 10.3 mmoles) was oxidized with 6.1 g (29 moles) of 82.2% m-chloroperbenzoic acid and the crude product was purified by chromatography on Silicar CC No. 7 with chloroform to give 1.3 g of 4-(4-methoxyphenyl)-2-(1,1,2,2-tetrafluoroethylsulfonyl)-5-(2-thienyl)-1H-imidazole, m.p. 163°-4.5° (recrystallized from chlorobutane).

Anal. Calc'd. for $C_{16}H_{12}F_4N_2O_3S_2$: C, 45.71; H, 2.86; N, 6.67. Found: C, 45.20; H, 2.92; N, 6.82.

EXAMPLE 10

4,5-bis-(2-Furyl)-2-(1,1,2,2-tetrafluoroethylthio)-1H-imidazole (A) 4,5-bis-(2-Furyl)-1H-2-imidazolethiol α-Furoin (19.2 g; 0.1 mole) was reacted with 11.5 g (0.15 mole) ammonium thiocyanate in ethanol heated at reflux to afford 11.4 g of 4,5-bis-(2-furyl)-1H-2-imidazolethiol. An analytical sample was prepared by chromatography on alumina with ethanol and recrystallization from nitromethane, m.p. 279°-380° (dec.).

Anal. Calc'd. for $C_{11}H_8N_2O_2S$: C, 56.90; H, 3.45; N, 12.07. Found: C, 57.20; H, 3.86; N, 11.72.

(B) 4,5-bis-(2-Furyl)-2-(1,1,2,2-tetrafluoroethylthio)-1H-imidazole.

4,5-bis-(2-Furyl)-1H-2-imidazolethiol (8.1 g; 39.4 mmoles) was reacted with 7.0 g of tetrafluoroethylene and the product purified by chromatography on Silicar CCNo. 7 with chloroform to give 3.0 g of 4,5-bis-(2-furyl)-2-(1,1,2,2-tetrafluoroethylthio)-1H-imidazole, m.p. 166°–167°: (recrystallized from 1-chlorobutane).

Anal. Calc'd. for $C_{13}H_8F_4N_2O_2S$: C, 47.99; H, 2.41; N, 8.43. Found: C, 47.13; H, 2.81; N, 8.45.

EXAMPLE 11

4-Phenyl-5-(3-pyridyl)-2-(1,1,2,2-tetrafluoroethylthio)-1H-imidazole.

(A) 4-Phenyl-5-(3-pyridyl)-1H-2-imidazolethiol

A solution of 30.0 g (0.15 mole) of 3-pyridyl benzyl ketone (A. Burger and C. R. Walter, Jr., J. Am. Chem. Soc., 72 1988 (1950), in 300 ml of acetic acid was treated dropwise with a solution of 25.0 g (0.16 mole) of bromine in 240 ml of acetic acid at room temperature. After stirring overnight, a precipitate of 26.8 g of 3-pyridyl α-bromobenzyl ketone hydrobromide was collected by filtration.

A mixture of 5.0 g (14.0 mmoles) of the salt above with a solution of 0.1 mole of sodium ethoxide in 100 ml of ethanol was stirred overnight at room temperature and then poured onto 0.5 M aqueous hydrochloric acid. After stirring for several hours the acidic aqueous solution was made basic with solid sodium carbonate and the product extracted into ether. The ether was dried over anhydrous potassium carbonate and removed under vacuum to give 4.5 g of 3-pyridyl α-hydroxybenzyl ketone.

Alternatively, a mixture of 20.0 g (56.0 mmoles) of 3-pyridyl α-bromobenzyl ketone hydrobromide and 24.0 g (0.24 mole) of potassium acetate in 100 ml of acetic anhydride was stirred overnight at room temperature. The reaction mixture was poured into water and the product extracted into ether. The combined ether layers were washed with water and then 10% aqueous sodium bicarbonate solution. The ether layer was dried over potassium carbonate and evaporated. A solution of the residue in 140 ml of 1 N aqueous hydrochloric acid was heated at reflux for 30 minutes and after cooling made basic with solid sodium carbonate. The product was extracted into ether and the combined ether extracts evaporated, after drying over anhydrous potassium carbonate, to give 8.15 g of 3-pyridyl α-hydroxybenzyl ketone.

3-Pyridyl α-hydroxybenzyl ketone (8.15 g; 38.3 mmoles) was reacted with 7.5 g (0.1 mole) of ammonium thiocyanate in 1-propanol heated at reflux to give 4.3 g of 4-phenyl-5-(3-pyridyl)-1H-2-imidazolethiol, m.p. 317°–323° recrystallized from $DMF:H_2O$ (2:1).

Anal. Calc'd. for $C_{14}H_{11}N_3S$: C, 66.40, H, 4.35; N, 16.60. Found: C, 65.92; 4.53; N, 16.34.

(B) 4-Phenyl-5-(3-pyridyl)-2-(1,1,2,2-tetrafluoroethylthio)-1H-imidazole

4-Phenyl-5-(3-pyridyl)-1H-2-imidazolethiol (2.0 g; 7.9 mmoles) was reacted with 5.0 g (50 mmoles) of tetrafluoroethylene and the crude product purified by chromatography on Silicar CCNo. 7 with chloroform to afford 800 mg of 4-phenyl 5-(3-pyridyl)-2-(1,1,2,2-tetrafluoroethylthio)-1H-imidazole, m.p. 153°–154° (recrystallized from toluene).

Anal. Calc'd. for $C_{16}H_{11}F_4N_3S$: C, 54.39; H, 3.12; N, 11.90. Found: C, 54.69; H, 3.37; N, 11.69.

Tables I and II illustrate other compounds that can be prepared by using the appropriate starting materials and the procedures described in the examples and in the Synthesis section.

TABLE I

| $y_1$ | $R_3$ | $R_1$ | $R_4$ | n |
|---|---|---|---|---|
| H | 3-pyridyl | $CF_3$ | H | 2 |
| $CH_3O$ | 2-thienyl | $CF_2CF_2H$ | H | 1 |
| F | 2-pyridyl | $CF_3$ | tetrahydropyranyl | 2 |
| F | 2-thienyl | $CF_2CF_2H$ | tetrahydrofuranyl | 2 |
| Cl | 2-thienyl | $CF_3$ | $CO_2CH_2$-phenyl | 0 |

TABLE I-continued
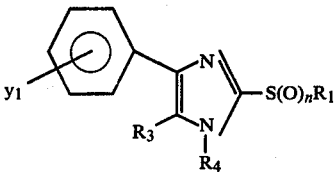
| y1 | R3 | R1 | R4 | n |
|---|---|---|---|---|
| CH3O— | 3-pyridyl | CF2H | H | 2 |
| F | 3-pyridyl | CF2CF2H | CH3OCH2— | 2 |
| Cl | 3-pyridyl | CF2CF2H | SO2—phenyl | 0 |
| F | 3-pyridyl N-oxide | CF3 | H | 2 |
| F | 3-pyridyl | CF2CF2H | H | 2 |
| CH3O | 2-thienyl | CF3 | H | 2 |
| F | 2-thienyl | CF3 | —C(O)—OC2H5 | 0 |
| F | 2-thienyl | CH2CF3 | H | 1 |
| CH3O— | 2-thienyl | CF2CH2F | —CH2—OCH2—phenyl | 2 |
| F | 2-furyl | CF2CHF2 | CO—phenyl | 0 |
| CH3O | 2-furyl | CF3 | H | 2 |
| F | 3-thienyl | CF2CHF2 | H | 2 |
| F | 3-thienyl | CF3 | H | 2 |
| F | 3-pyridyl | CF2CHF2 | COCH3 | 0 |

TABLE II $$R_2, R_3 \text{ on pyrazole with } R_1\text{-S(O)}_n, R_4 \text{ on N}$$

| R2, R3 | R1 | R4 | n |
|---|---|---|---|
| thiophene (S) | CF2CF2H | SO2-phenyl | 0 |
| pyridine (N) | CF2CF2H | H | 0 |
| pyridine (N) | CF3 | H | 2 |
| pyridine N-oxide | CF3 | H | 2 |
| pyridine (N) | CF2CF2H | H | 2 |
| thiophene (S) | HCF2 | H | 2 |
| thiophene (S), pyridine (N) | CF3 | CO2CH3 | 0 |
| thiophene (S), pyridine (N) | CF2CF2H | H | 0 |
| furan (O), thiophene (S) | CF2CHF2 | H | 0 |

Dosage Forms

The anti-arthritic and analgesic agents of this invention can be administered to treat arthritis and/or pain by any means that produces contact of the active agent with the agent's site of action in the body of a mammal. The compounds of formula I have anti-arthritic properties and in addition some can be used to alleviate pain. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 40 milligrams per kilogram of body weight. Ordinarily 0.05 to 20, and preferably 0.1 to 10 milligrams per kilogram per day given in divided doses 2 to 4 times a day or in sustained release form is effective to obtain desired results.

Dosage forms (compositions) suitable for internal administration contain from about 0.1 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective distintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkanium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 10 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Injectable

A parenteral composition suitable for administration by injection is prepared by dissolving 1% by weight of active ingredient in sodium chloride injection U.S.P. XV and adjusting the pH of the solution to between 6 to 7. The solution is sterilized by filtration.

Use

To detect and compare the anti-inflammatory activities of compounds in this series and standard drugs, a test was used based on a standard model of arthritis for which there is good correlation with human efficacy. The model is adjuvant-induced arthritis in rats. Federation Proceedings, Vol. 32, No. 2 1973 "Models Used for the Study and Therapy of Rheumatoid Arthritis"-Symposium of the American Society for Pharmacology and Experimental Therapeutics-states "The rat polyarthritis produced by intradermal injection of a suspension of *Mycobacterium tuberculosis* in mineral oil (adjuvant) has been used extensively for the screening of drugs of potential use in rheumatoid arthritis."

Established Adjuvant-Induced Arthritis in Rats

Charles River Lewis male rats (130–150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Nonarthritic controls are injected with mineral oil. The animals are held for two weeks to allow development of arthritis. Paw volumes (uninjected, left hind paw) are measured and the adjuvant injected rats are culled and distributed to treatment groups of 10 of equal disease severity. Nonarthritic controls are distributed to two groups of 10. The rats are given oral doses of compound or PVA-Acacia (Polyvinyl Alcohol 1%, Gum Acacia, U.S.P. 5%, Methylparaben 0.5%) (10 ml/kg) by gavage on that day and on the six following days. One day after the last dose the paw volumes (uninjected, left hind paw) are measured using a Ugo Basile Volume Differential Meter Model 7101.

$$\frac{\text{Arthritic Control} \quad \text{Treatment Group}}{\text{Mean Paw Volume (ml)} - \text{Mean Paw Volume (ml)}} \times 100 =$$
$$\frac{\text{Arthritic Control} \quad \text{Non-Arthritic Control}}{\text{Mean Paw Volume (ml)} - \text{Mean Paw Volume (ml)}}$$

% Decrease from Control Mean Paw Volume.

Dose-response regression lines of the percent decrease are plotted on semi-log paper by visual fit and the ED50% decrease from control paw volume is determined by inspection. Data for some of the compounds in this invention are summarized in Table III.

Compounds from this series are many times more potent than aspirin and ibuprofen in the treatment of adjuvant induced arthritis in rats. Four compounds have been shown to be more potent than phenylbutazone and one compound has been shown to be more potent than indomethacin in this test system.

TABLE III

| Established Adjuvant-Induced Arthritis in Rats (A.A.) | |
|---|---|
| Chemical Example Number | A. A. ED50%* mg/kg |
| 1 | 32% at 50 mg/kg |
| 2 | 1.3 |
| 3 | 0.1 |
| 4 | 12.0 |
| 5 | 2.2 |
| 6 | 50 |
| 8 | 30 |
| 9 | 5 |
| 10 | 34% at 50 mg/kg |
| 11 | <25 |
| Indomethacin | 0.3 |
| Phenylbutazone | 10 |
| Ibuprofen | 100 |
| Aspirin | 305 |

*Determined as % paw volume reduction from control.

Phenylquinone Writhing Test

A standard procedure for detecting and comparing the analgesic activity of compounds in this series for which there is good correlation with human efficacy is the standard phenylquinone writhing test modified from Siegmund, et al., *Proc. Soc. Exp. Biol. Med.* 95, 729 (1957). A test compound suspended in 1% methylcellulose was given orally to fasted (17–21 hours) female white mice, 5–20 animals per double blind test. Aqueous (0.01% phenyl-p-benzoquinone) phenylquinone was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.* 11, 115–145 (1947); also time of peak action was determined for many of the compounds. This data is summarized in Table IV.

TABLE IV

| Phenylquinone Writhing Test | |
|---|---|
| Chemical Example Number | $ED_{50}$* |
| 1 | 4.6 |
| 3 | 2.1 |
| 5 | <130 |
| 8 | 45 |
| 9 | 1.67 |

*units are in mg/kg at ½ hour.

We claim:

1. A compound of the formula

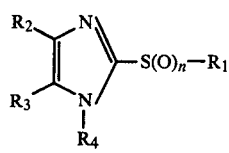

where
n=0, 1, or 2;
$R_1$ = polyfluoro-$C_1$—$C_2$ alkyl;
$R_2$ and $R_3$, the same or different = 2-thienyl, 3-thienyl, 3-pyridyl, 3-pyridyl-N→oxide, 2-furyl or

where
$Y_1$ and $Y_2$, the same or different = H, $C_1$-$C_4$ alkoxy, $C_1$-$C_4$ alkyl, Cl, F, or $Y_1$ and $Y_2$ taken together forming a dioxymethylene bridge,
provided that only one of $R_2$ or $R_3$ can =

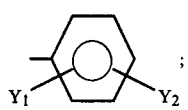

and
$R_4$ = hydrogen;

2-tetrahydropyranyl,
2-tetrahydrofuranyl,

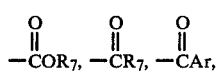

or —$SO_2Ar$;
where
$R_5$ = H or methyl;
$R_6$ = $C_1$-$C_3$ alkyl, benzyl, —$CH_2CH_2OCH_3$

$R_7$ = $C_1$-$C_4$ alkyl or benzyl; and

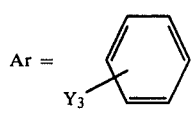

where
$Y_3$ = H, F, Cl, Br, $C_1$-$C_4$ alkyl $C_1$-$C_4$ alkoxy or nitro; provided when

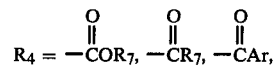

or —$SO_2Ar$,
then n must be 0; or
its pharmaceutically suitable acid addition salt where n=0 or where at least one of $R_2$ or $R_3$, independently, = 3-pyridyl or its pharmaceutically suitable metal salt where $R_4$ = hydrogen and n = 1 or 2.

2. A compound of claim 1 where $R_1$ = —$CF_2CF_2H$ or —$CF_3$.

3. A compound of claim 1 where $R_2$ and $R_3$, independently = 2-thienyl or 3-pyridyl.

4. A compound of claim 1 where $R_2$ or

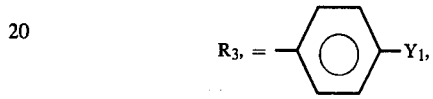

where $Y_1$ = H, Cl, F, or $CH_3O$.

5. A compound of claim 1 where $R_4$ = hydrogen, ethoxycarbonyl, benzyloxymethyl, acetyl, benzoyl or 2-tetrahydrofuranyl.

6. A compound of claim 4 where $R_4$ = hydrogen.

7. A compound of claim 1 where $R_1$ = —$CF_2CF_2H$ or —$CF_3$; $R_2$ and $R_3$, independently, = 2-thienyl, or 3-pyridyl, or

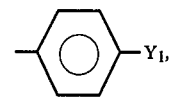

where $Y_1$ = H, Cl, F or $CH_3O$, provided that only one of $R_2$ or $R_3$

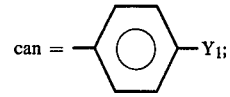

and $R_4$ = hydrogen, benzyloxymethyl, acetyl, benzoyl, or 2-tetrahydrofuranyl.

8. The compound of claim 1 which is 4-(4-fluorophenyl)-2-(1,1,2,2-tetrafluoroethylsulfonyl)-5-(2-thienyl)-1H-imidazole.

9. The compound of claim 1 which is 4-(4-fluorophenyl)-5-(2-thienyl)-2-trifluoromethylsulfonyl-1H-imidazole.

10. The compound of claim 1 which is 4-(4-methoxyphenyl)-4-(2-thienyl)-2-trifluoromethylsulfonyl-1H-imidazole.

11. The compound of claim 1 which is 4,5-bis-(2-thienyl)-2-(1,1,2,2-tetrafluoroethylsulfonyl)-1H-imidazole.

12. The compound of claim 1 which is 4-(4-methoxyphenyl)-2-(1,1,2,2-tetrafluoroethylsulfonyl)-5-(2-thienyl)-1H-imidazole.

13. The compound of claim 1 which is 4-(3,4-dichlorophenyl)-2-(1,1,2,2-tetrafluoroethylsulfonyl)-5-(2-thienyl)-1H-imidazole.

14. A pharmaceutical composition comprising a suitable pharmaceutical carrier and an effective antiarthritic amount of the compound of claim 1.

15. A pharmaceutical composition comprising a suitable pharmaceutical carrier and an effective antiarthritic amount of the compound of claim 2.

16. A pharmaceutical composition comprising a suitable pharmaceutical carrier and an effective antiarthritic amount of the compound of claim 3.

17. A pharmaceutical composition comprising a suitable pharmaceutical carrier and an effective antiarthritic amount of the compound of claim 4.

18. A pharmaceutical composition comprising a suitable pharmaceutical carrier and an effective antiarthritic amount of the compound of claim 5.

19. A pharmaceutical composition comprising a suitable pharmaceutical carrier and an effective antiarthritic amount of the compound of claim 6.

20. A pharmaceutical composition comprising a suitable pharmaceutical carrier and an effective antiarthritic amount of the compound of claim 7.

21. A pharmaceutical composition comprising a suitable pharmaceutical carrier and an effective antiarthritic amount of the compound of claim 8.

22. A pharmaceutical composition comprising a suitable pharmaceutical carrier and an effective antiarthritic amount of the compound of claim 9.

23. A pharmaceutical composition comprising a suitable pharmaceutical carrier and an effective antiarthritic amount of the compound of claim 10.

24. A pharmaceutical composition comprising a suitable pharmaceutical carrier and an effective antiarthritic amount of the compound of claim 11.

25. A pharmaceutical composition comprising a suitable pharmaceutical carrier and an effective antiarthritic amount of the compound of claim 12.

26. A pharmaceutical composition comprising a suitable pharmaceutical carrier and an effective antiarthritic amount of the compound of claim 13.

27. A method of treating arthritis in a mammal in need of treatment which comprises administering to the mammal an effective anti-arthritic amount of the compound of claim 1.

28. A method of treating arthritis in a mammal in need of treatment which comprises administering to the mammal an effective anti-arthritic amount of the compound of claim 2.

29. A method of treating arthritis in a mammal in need of treatment which comprises administering to the mammal an effective anti-arthritic amount of the compound of claim 3.

30. A method of treating arthritis in a mammal in need of treatment which comprises administering to the mammal an effective anti-arthritic amount of the compound of claim 4.

31. A method of treating arthritis in a mammal in need of treatment which comprises administering to the mammal an effective anti-arthritic amount of the compound of claim 5.

32. A method of treating arthritis in a mammal in need of treatment which comprises administering to the mammal an effective anti-arthritic amount of the compound of claim 6.

33. A method of treating arthritis in a mammal which comprises administering to the mammal in need of treatment an effective anti-arthritic amount of the compound of claim 7.

34. A method of treating arthritis in a mammal in need of treatment which comprises administering to the mammal an effective anti-arthritic amount of the compound of claim 8.

35. A method of treating arthritis in a mammal in need of treatment which comprises administering to the mammal an effective antiarthritic amount of the compound of claim 9.

36. A method of treating arthritis in a mammal in need of treatment which comprises administering to the mammal an effective antiarthritic amount of the compound of claim 10.

37. A method of treating arthritis in a mammal in need of treatment which comprises administering to the mammal an effective anti-arthritic amount of the compound of claim 11.

38. A method of treating arthritis in a mammal in need of treatment which comprises administering to the mammal an effective anti-arthritic amount of the compound of claim 12.

39. A method of treating arthritis in a mammal in need of treatment which comprises administering to the mammal an effective anti-arthritic amount of the compound of claim 13.

* * * * *